(12) United States Patent
Huo

(10) Patent No.: US 7,840,055 B2
(45) Date of Patent: Nov. 23, 2010

(54) COMPUTER AIDED TUBE AND TIP DETECTION

(75) Inventor: Zhimin Huo, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 1005 days.

(21) Appl. No.: 11/644,858

(22) Filed: Dec. 22, 2006

(65) Prior Publication Data

US 2008/0118140 A1    May 22, 2008

Related U.S. Application Data

(60) Provisional application No. 60/860,300, filed on Nov. 21, 2006.

(51) Int. Cl.
*G06K 9/00* (2006.01)
(52) U.S. Cl. ............................. 382/132; 382/128
(58) Field of Classification Search ......... 382/128–132; 600/437
See application file for complete search history.

(56) References Cited

U.S. PATENT DOCUMENTS

| | | | |
|---|---|---|---|
| 2003/0053697 A1* | 3/2003 | Aylward et al. | 382/203 |
| 2003/0135115 A1* | 7/2003 | Burdette et al. | 600/437 |
| 2004/0109594 A1 | 6/2004 | Luo et al. | |

OTHER PUBLICATIONS

Nodine et al. ("Observer performance in the localization of Tubes and Catheters on Digital chest images: The role of expertise and image enhancement", Academic Radiology, vol. 3, No. 10, Oct. 1, 1996, pp. 834-841, XP005306278).*
Calvin F. Nodine et al., "Observer Performance in the Localization of Tubes and Catheters on Digital Chest Images: The Role of Expertise and Image Enhancement," Academic Radiology, vol. 3, No. 10, Oct. 1, 1996, pp. 834-841, XP005306278.
J. Illingworth et al., "A Survey of the Hough Transform," Computer Vision Graphics and image Processign, Academic Press, vol. 44, No. 1, Oct. 1, 1988, pp. 87-116, XP000008809.
Steffen Weiss et al., "Ein Verfahren zur sicheren Visualisierung and Lokalisierung von Kathertern für MR-geführte intravaskuläre Prozeduren," Zeitschrift Fuer Medizinische Physik, Urban Und Fischer, vol. 13, No. 3, Jan. 1, 2003, pp. 172-176, XP009027858.

* cited by examiner

*Primary Examiner*—Vu Le
*Assistant Examiner*—Amara Abdi

(57) ABSTRACT

A computer aided tube and tip detection method for a radiographic image. Radiographic image data is obtained, and a region of interest in the image is determined. The image is processed to provide edge enhancements forming an edge-enhanced image. Edge segments in the edge-enhanced image are detected. Connected lines from the edge segments are formed to obtain a set of connected lines. A tube structure is identified by pairing one or more pairs of connected lines that are separated by a width dimension in a predetermined range. A tip is detected for the tube structure according to the convergence or divergence of paired connected lines.

16 Claims, 23 Drawing Sheets

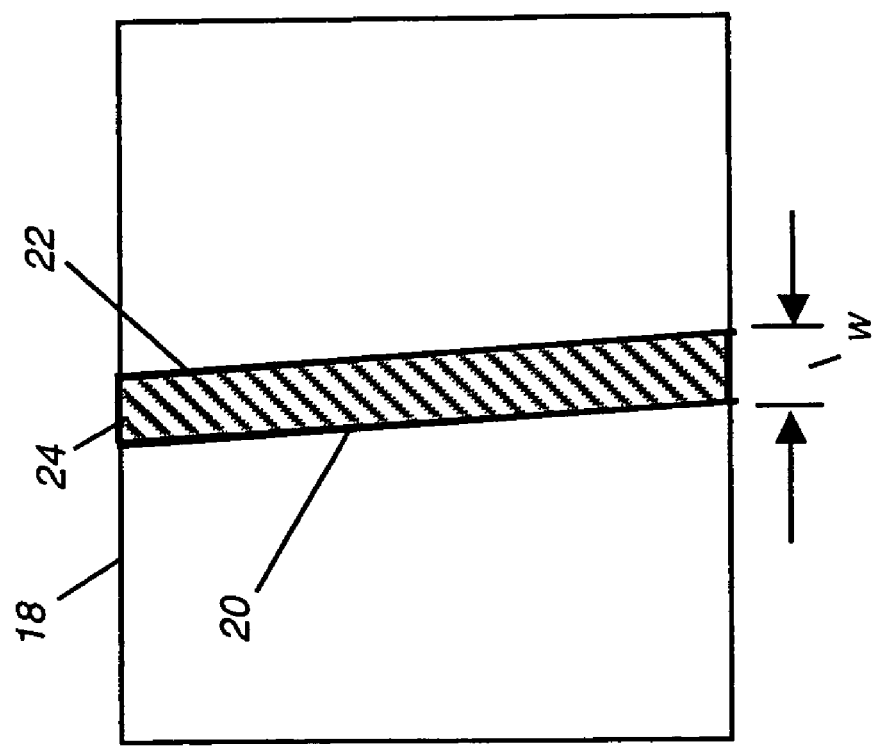

The left and right points for point A are determined based on its gradient direction $A\_\theta$

- If $A\_\theta < 25°$ then points left0 and right0 are its left and right sides
- If $25° \leq A\_\theta < 50°$, then left1 and right1 are its left and right sides.
- If $50° \leq A\_\theta < 75°$, then left2 and right2 are its left and right sides.
- If $A\_\theta \geq 75°$, then left3 and right3 are its left and right sides.

| Right2 | Right3 | Right1 |
|--------|--------|--------|
| Left0  | A      | Right0 |
| Left1  | Left3  | Left2  |

Criteria used for determining A value in the output binary image. The determination is based on the gradient value of A relative to its 8 neighboring points and the thresholds $T_1$ and $T_2$.

- If the gradient of A is smaller than left and right sides, the A point value is 0 in the binary edge image.
- Else if the gradient value of A is smaller than $T_1$, the A point value is 0 in the binary edge image.
- Else if the gradient value of A is larger than $T_2$, the A point value is 1 in the binary edge image.
- Else if any one among A's 8-Neighbor is larger than $T_2$, the A point value is 1 in the binary image, else is 0.

*FIG. 12*

COMPUTER AIDED TUBE AND TIP DETECTION

CROSS REFERENCE TO RELATED APPLICATION

Reference is made to and priority claimed from U.S. Provisional Application Ser. No. 60/860,300, filed Nov. 21, 2006, entitled COMPUTER-AIDED TUBE AND TIP DETECTION.

FIELD OF THE INVENTION

This invention generally relates to processing of diagnostic images and more particularly to a method and system for enhancing diagnostic images to detect the position of tubes positioned within the patient.

BACKGROUND OF THE INVENTION

Clinical evaluation of patients in an Intensive Care Unit (ICU) often relies heavily on diagnostic images, such as portable chest radiographic images, for example. It is noted that chest radiographs can be particularly helpful in the ICU for indicating significant or unexpected conditions requiring changes in patient management. To meet the need for readily accessible and rapid diagnostic imaging, equipment such as portable chest radiography equipment has been developed, allowing the ICU clinician to conveniently obtain a radiographic image as needed for the patient.

A concern for effective patient treatment relates to the ability to detect the proper positioning of tubes that have been inserted into the patient. These include, for example, endotracheal (ET) tubes, FT tubes, and NT tubes. Proper tube positioning can help to insure delivery or disposal of liquids and gases to and from the patient during a treatment procedure. Improper tube positioning can cause patient discomfort, render a treatment ineffective, or can even be life-threatening. However, even though tubing, wires, and other apparatus used to support the patient appear in a radiographic image, little or no attention has been paid to using this fact to assist patient treatment. Image processing techniques are directed more to eliminating unwanted effects of tube positioning in the obtained image than to the task of tube detection and identification. There is, then, a need for a diagnostic imaging method for detecting and identifying tube position and type.

SUMMARY OF THE INVENTION

The present invention provides computer aided tube and tip detection method for a radiographic image. According to one aspect of the present invention, a radiographic image data is obtained and a region of interest in the image is determined. The image is processed to provide edge enhancements forming an edge-enhanced image. Edge segments in the edge-enhanced image are detected. Connected lines from the edge segments are formed to obtain a set of connected lines. A tube structure is identified by pairing one or more pairs of connected lines that are separated by a width dimension in a predetermined range. A tip is detected for the tube structure according to the convergence or divergence of paired connected lines.

The present invention provides a method for detecting and identifying one or more types of tubing from radiological image data.

The present invention adapts to different imaging apparatus and equipment, so that images taken at different times or on different imaging systems can be processed and compared.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings.

FIGS. 10A, 10B, and 10C show edge detection used for identifying a tube structure.

FIG. 12 is a logic diagram showing edge detection logic steps.

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

The present invention provides a method for automated detection of tubing and tube tips from a radiographic image. The method of the present invention detects and connects edge segments from an enhanced image to detect a pair of lines that indicate one or more types of tubing and further analyzes tubing lines in order to detect the tip of each tube.

Figure 1:
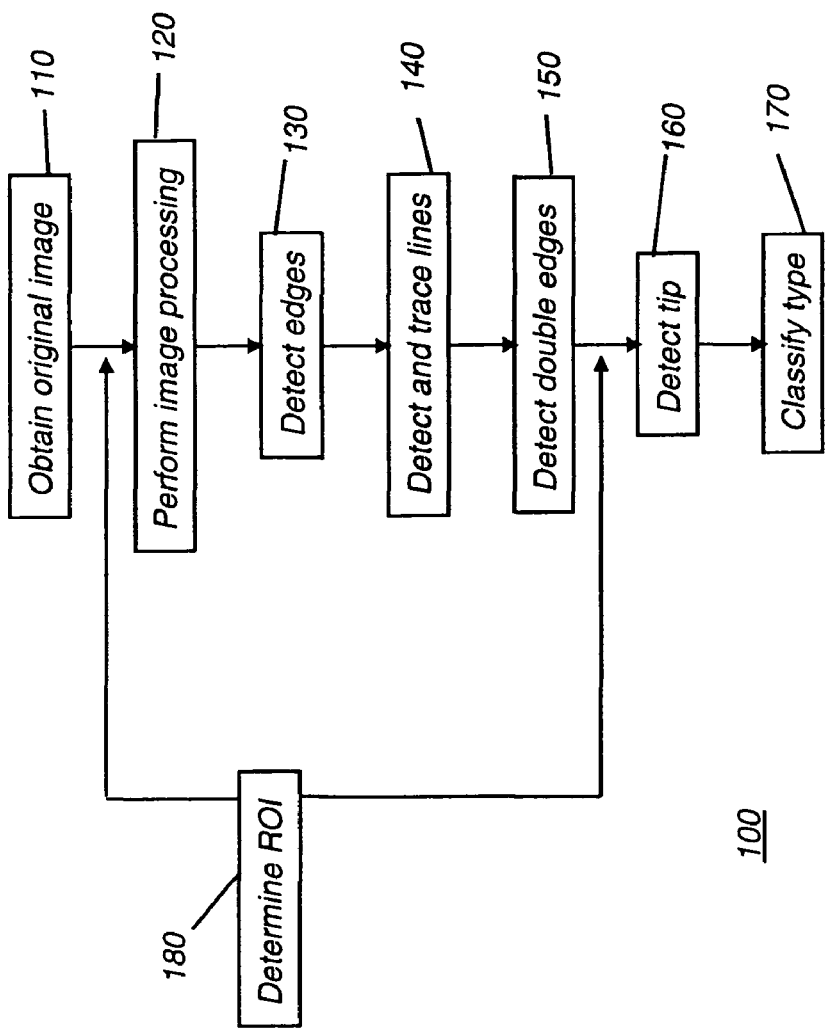
FIG. 1 is a logic flow diagram showing a basic sequence for tube and tip detection in embodiments of the present invention.

FIG. 1 is a flow diagram of a detection method 100 showing a basic sequence for tube and tip detection in embodiments of the present invention. In an obtain image step 110, the diagnostic image data for the patient is obtained, such as from a digital radiography (DR or CR) system or from a scanner, for example. An optional image processing step 120 can be helpful for performing any necessary cleanup and noise removal that might be helpful. An edge detection step 130 then performs the processing needed in order to detect edges for objects and structures in the image field. The subsequent line detection and tracing step 140 applies imaging algorithms to the problem of locating peripheral edges of tubing and other objects in the image field. A double edge detection step 150 follows, in which parallel edges of structures are identified. A tip detection step 160 can then be carried out for identifying the end of the tip structure. A classification step 170 is then executed to identify the type of tubing. A ROI determination step 180 can be carried out at a number of different points of the sequence, such as prior to image processing step 120 or just following double edge detection step 150.

Figure 2:
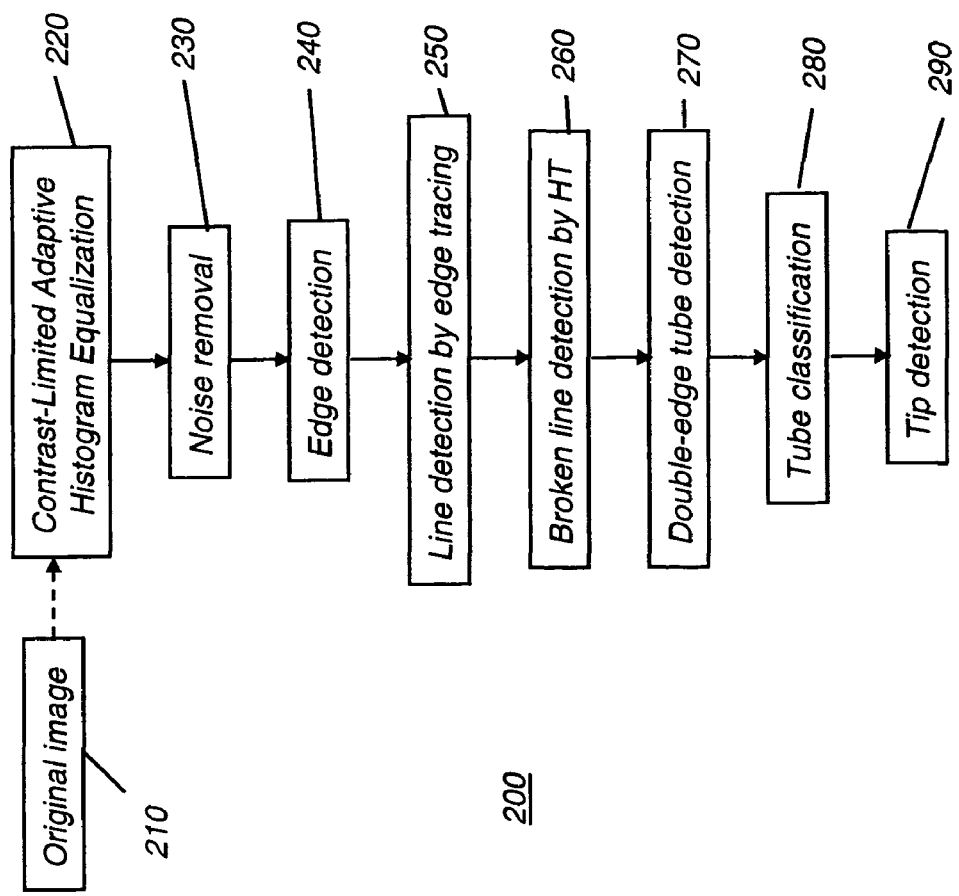
FIG. 2 is a logic flow diagram showing a tube and tip detection sequence according to one embodiment.
Figure 3:
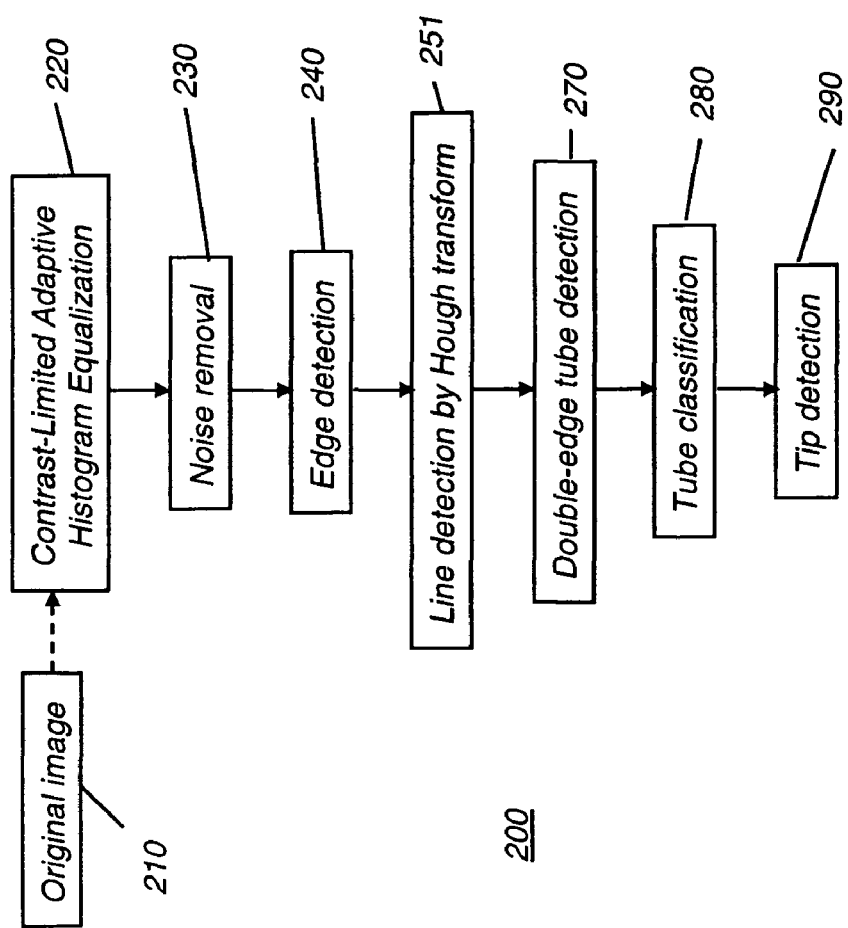
FIG. 3 is a logic flow diagram showing a tube and tip detection sequence according to an alternative embodiment.
Figure 5:
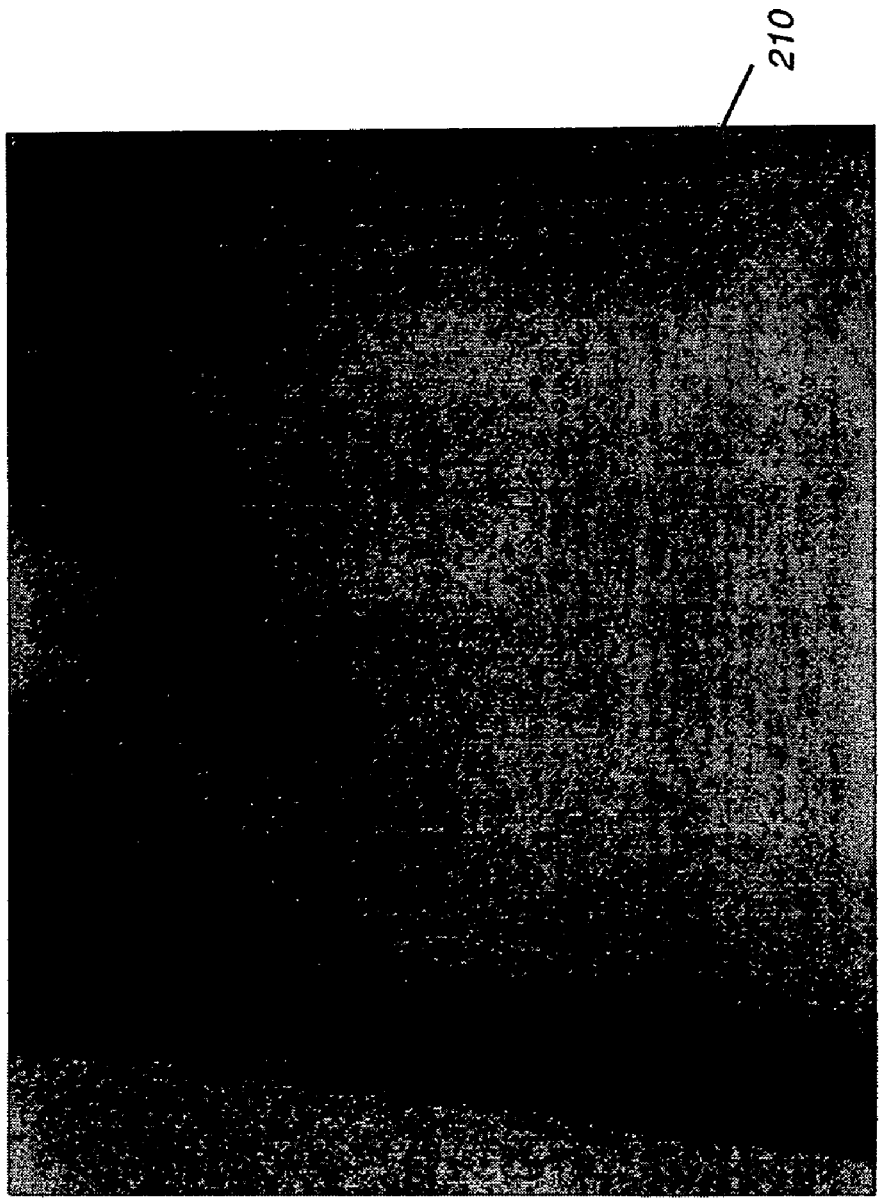
FIG. 5 is an original x-ray image.
Figure 6:
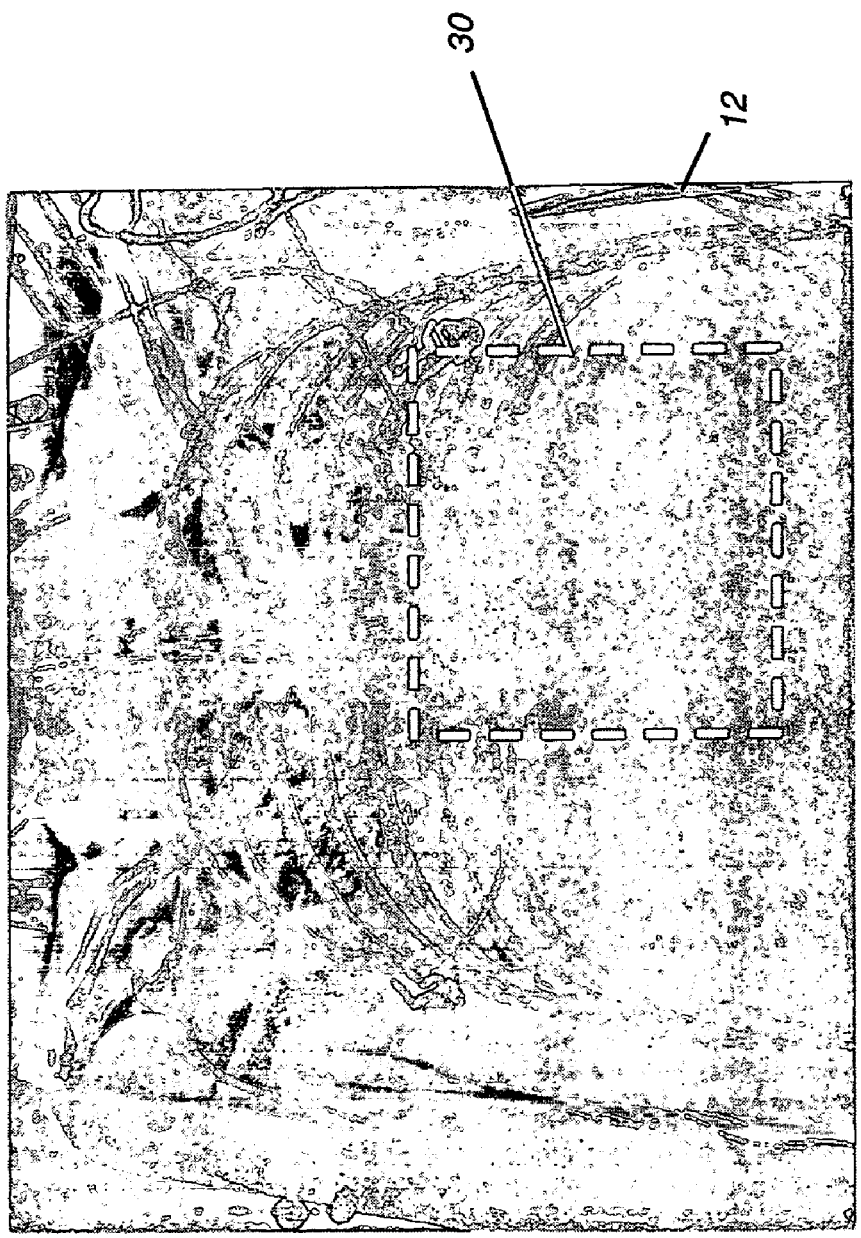
FIG. 6 is a processed x-ray image.
Figure 7:
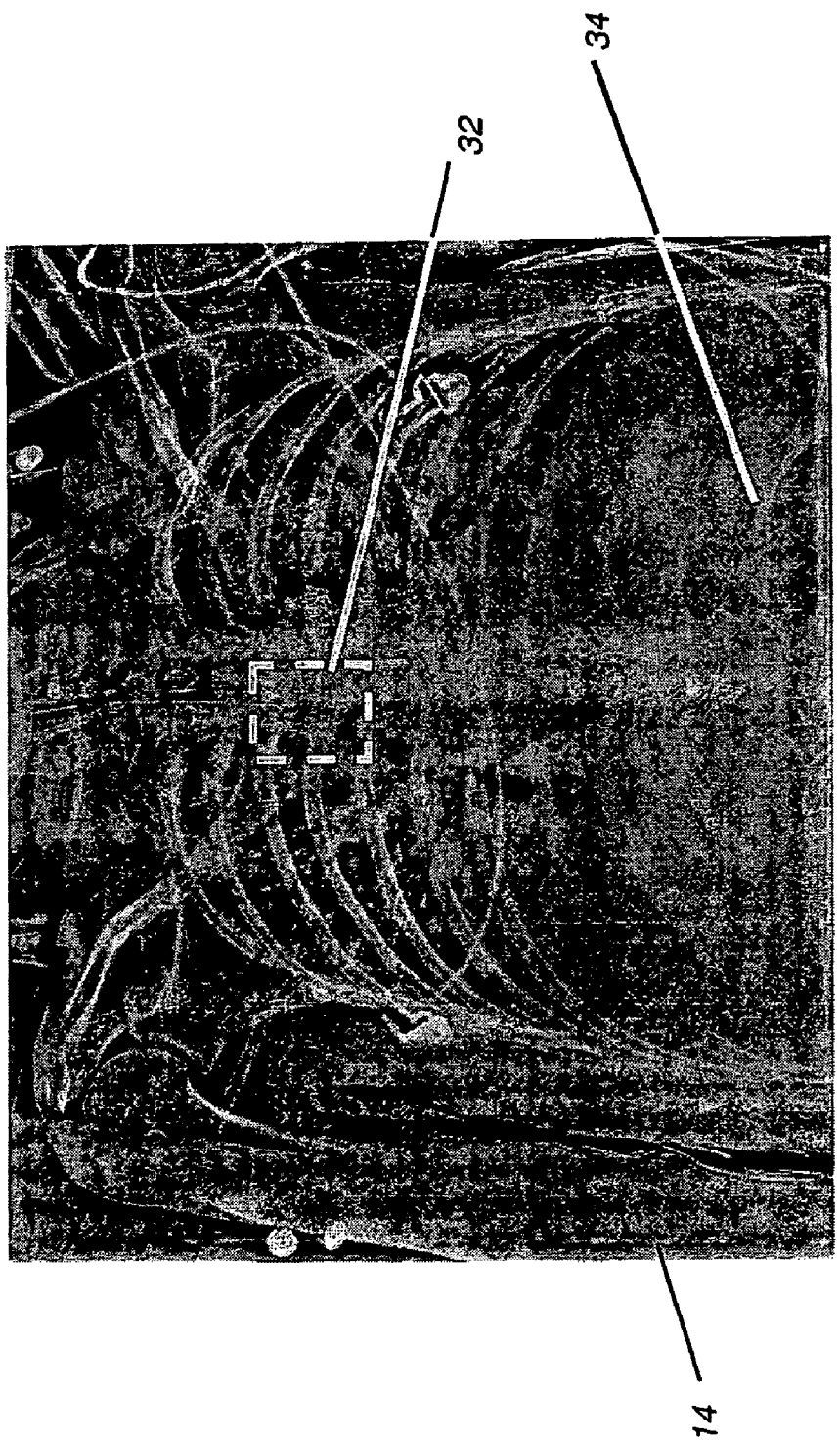
FIG. 7 is a processed x-ray image showing a tube outline.

FIGS. 2 and 3 show logic flow diagrams for two embodiments of the method of the present invention. Referring first to the embodiment of FIG. 2, a detection method 200 takes as its input the image data from an original radiography image 210. As shown in FIG. 5, original image 210 may be relatively indistinct, requiring some amount of processing in order to enhance contrast so that features such as skeletal and other tissue structures as well as tubing and other items can be visible. To provide this enhancement, a histogram equalization step 220 is first performed to enhance the contrast of the grayscale image by transforming values using Contrast-Limited Adaptive Histogram Equalization (CLAHE), described in more detail subsequently, or using some other suitable method. FIG. 6 shows an enhanced image 12 provided using CLAHE processing. An area 30 is outlined in dotted line rectangle to indicate a high noise area of the processed image. A noise removal step 230 follows, reducing the effects of noise on the image. Conventional techniques can be used for noise removal, such as using a Gaussian or anisotropic filter, for example. Noise removal step 230 provides a reduced noise image 14 as shown in FIG. 7. An outlined area 32 indicates the region of interest (ROI) that includes an ET tube tip. An FT tube 34 is disposed at the noted location in FIG. 7.

Figure 8:
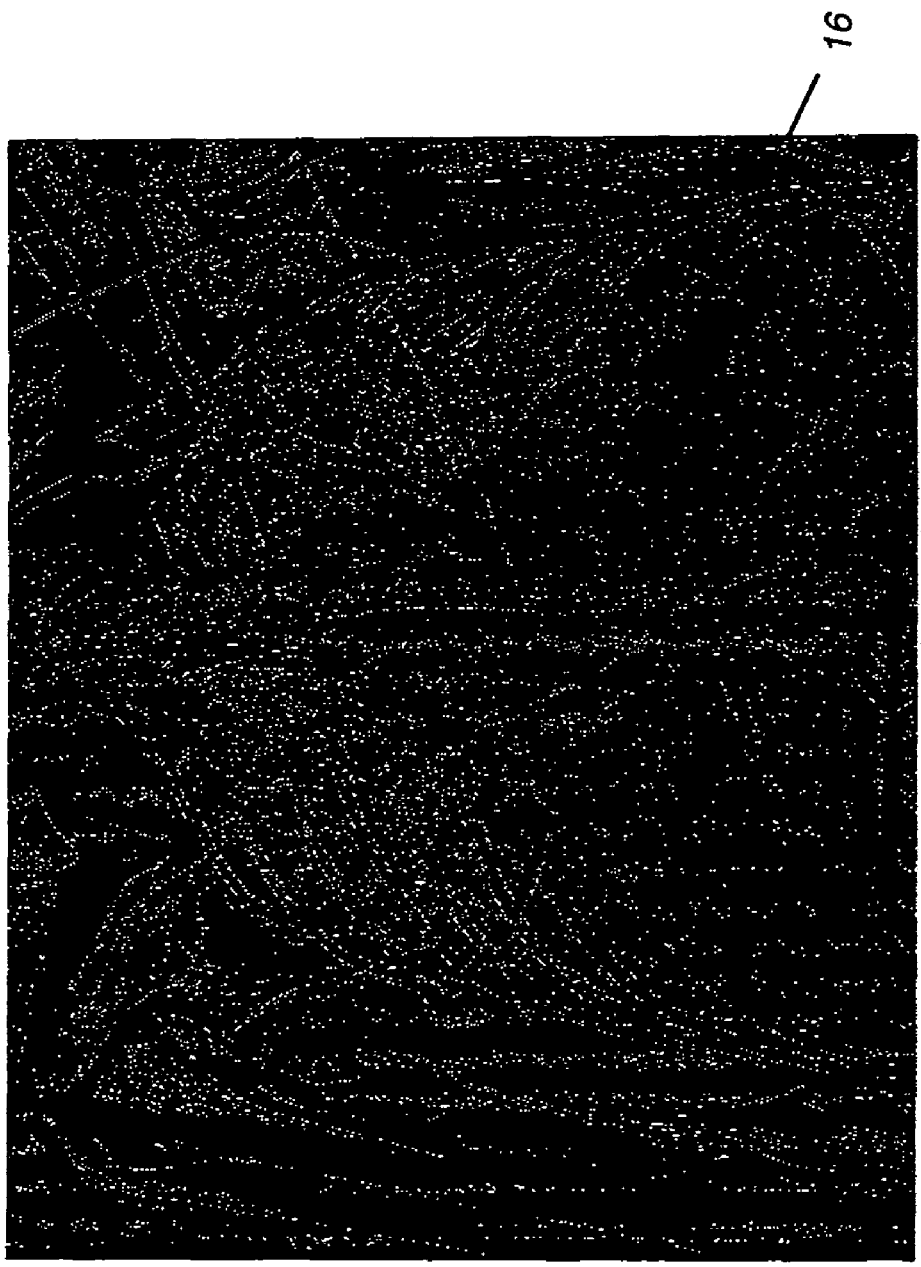
FIG. 8 is an image obtained using Canny edge detection.

Still following the process of FIG. 2, an edge detection step 240 follows. In one embodiment, Canny edge detection is used, as described in more detail subsequently. Canny edge detection is well known to those skilled in the image processing arts. FIG. 8 shows an image 16 that has been processed using Canny edge detection, showing slight linear patterns that may indicate skeletal features such as ribs or spine or may indicate tubing. A first line detection step 250 detects these lines from the Canny resultant image 16, using edge tracing. A second line detection step 260 then detects broken lines or line segments and reconstructs lines from these segments, using a Hough Transform, well known to those skilled in the image processing arts. A tube detection step 270 then detects the tube structure using a double-edge detection scheme, described in more detail subsequently. A classification step 280 is then executed, in which the type of tube can be determined based on thickness and relative location. A tip detection step 290 is finally carried out, determining the location of the tip of the tube.

Figure 9:
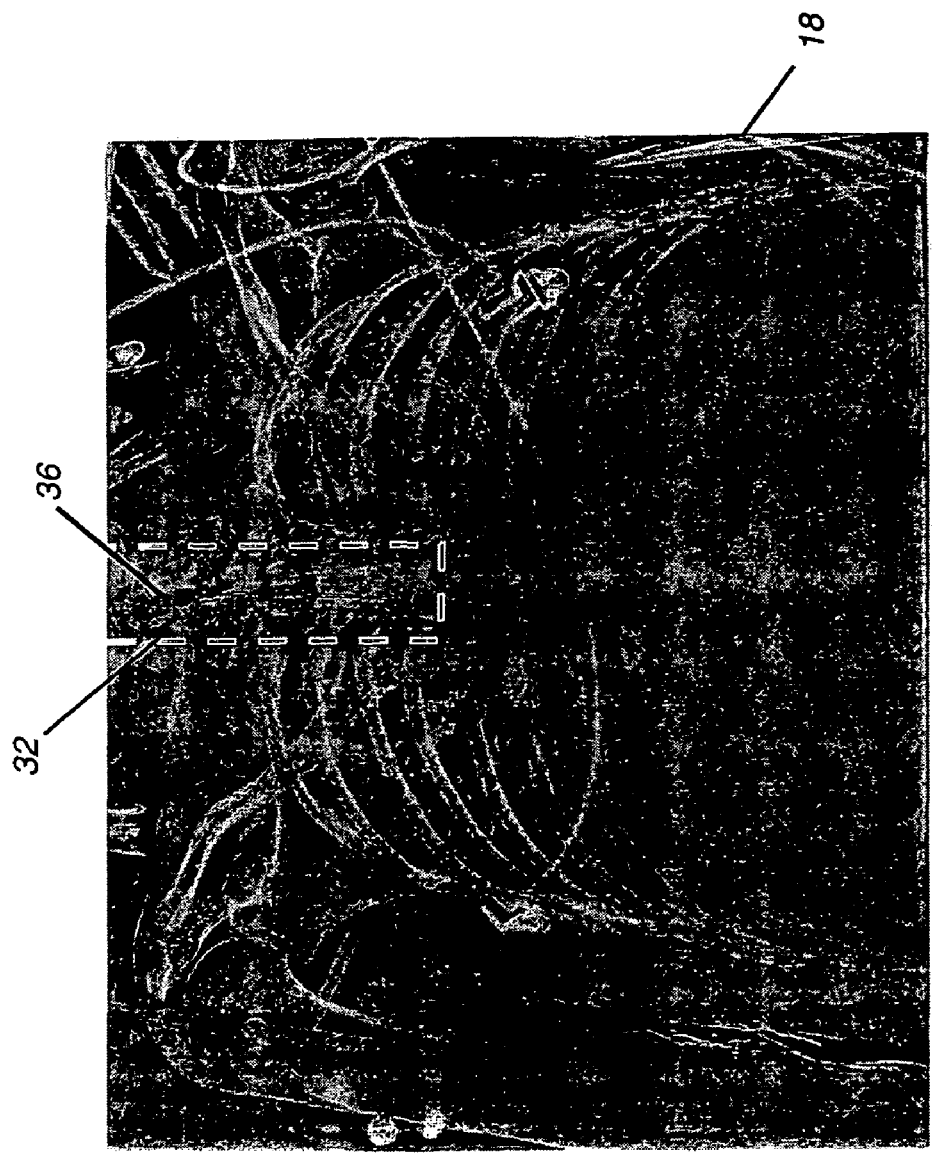
FIG. 9 is an image showing an outline of an endo-tracheal tube.

FIG. 9 shows an example with tube 36 identified within a processed image 18. Area 32, shown in dotted outline, indicates the ROI.

Histogram Equalization

Figure 11:
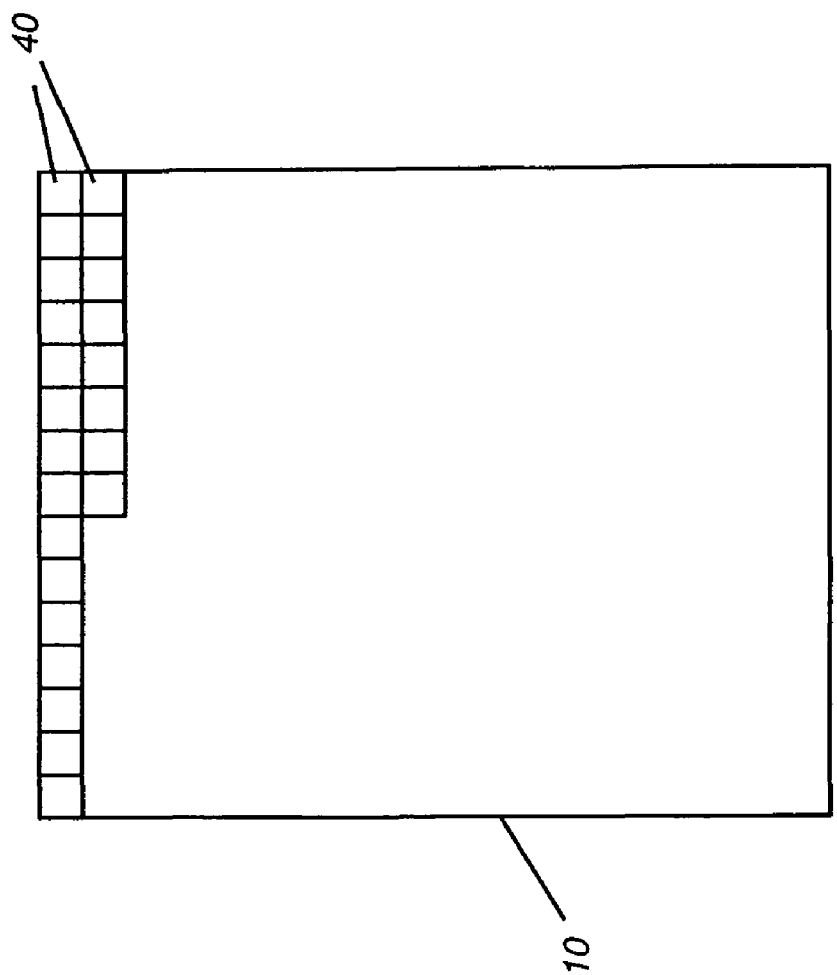
FIG. 11 is a plan view showing a tiling arrangement.

As noted earlier, Contrast-Limited Adaptive Histogram Equalization (CLAHE) is one method available for enhancing the contrast of the grayscale image. Rather than operating on the entire image, the CLAHE method operates most effectively on small regions in the image, called tiles, suitably dimensioned. One typical tile size is 30×30 pixels, for example. FIG. 11 shows one example arrangement of tiles 40 in an image 10. Each tile's contrast can be enhanced, so that the histograms of the output regions approximately match a specified histogram. Neighboring tiles are then combined using bilinear interpolation to eliminate artificially induced boundaries. Contrast, especially in homogeneous areas, can be constrained to avoid unwanted amplification of noise.

Edge and Line Detection

Figure 4:
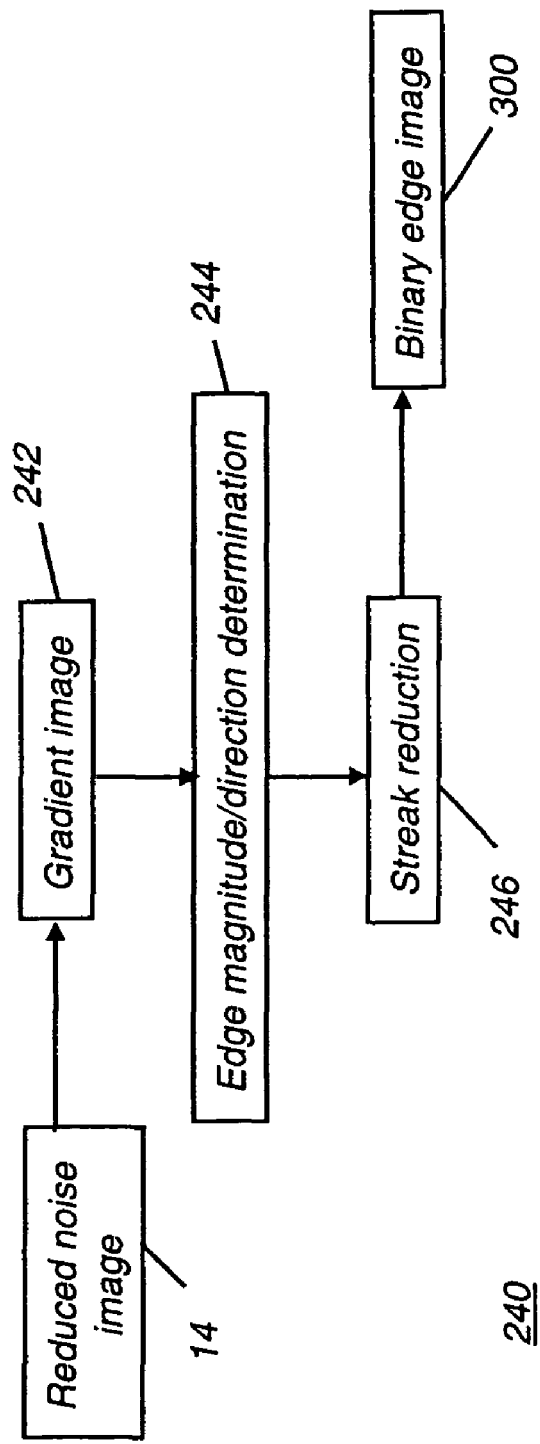
FIG. 4 is a logic flow diagram showing edge detection steps.

The logic flow diagram of FIG. 4 shows edge detection step 240, using Canny edge detection in one embodiment. The overall goal of edge detection step 240 is to identify edges within the image that are relatively pronounced and unbroken, that display within a given region of interest (ROI), and that are generally vertical. Reduced noise image 14 is first processed to calculate gradient data in a gradient calculation step 242. In one embodiment, this calculation uses kernels of various size 3×3, 5×5, 7×7, or 13×13, for example. The gradients along the x and y directions, Gx and Gy respectively, are calculated for each point. The direction for the gradient G (Gx, Gy) is determined by:

$$\theta = \tan^{-1}(Gy/Gx).$$

For an edge detection step 244, the left edge of the tube can then be determined from the image using Gx. Using the −Gx value then enables the right edge of the tube to be located.

FIG. 12 shows a gradient map that is used for edge determination criteria at each pixel A in the image. Decision criteria used in one embodiment are also shown in FIG. 12. Whether or not a point qualifies as an edge point is determined based on the gradient value at A relative to the gradient values of its 8 neighboring points and the thresholds $T_1$ and $T_2$.

The thresholds $T_1$ and $T_2$ applied to the gradient image can be computed as follows:

$$T_1 = 0.5(\text{Avg})$$

$$T_2 = 1.0(\text{Avg})$$

where Avg is the average gradient for the whole image. The edge detection algorithms are applied over a given region of interest (ROI), rather than over the whole image. The ROI for each type of image and the types of tubes inserted into the patient are known in advance; taking advantage of this information allows optimization of the detection algorithms used in the method of the present invention. In addition, it is noted that the use of earlier results for the same patient can be provided to the system of the present invention, so that the location of tubes from images taken on a previous day, for example, can be used as hints for the search algorithms.

Figure 13:
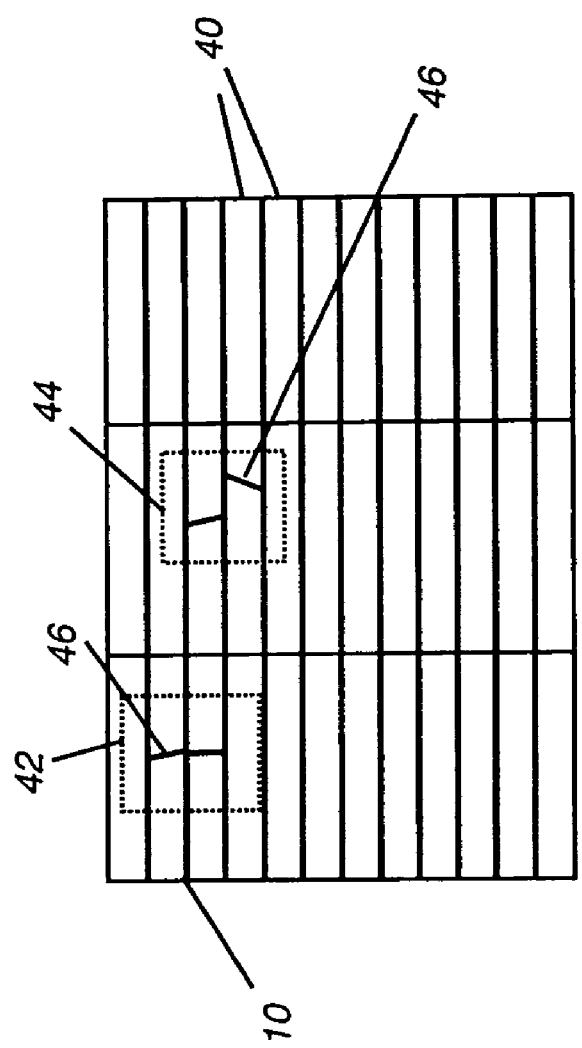
FIG. 13 is a plan view of a tiled image showing detected line segments.

Referring to FIG. 13, line detection when using tiling attempts to identify line edges that have similar direction and are close to line edges in adjacent tiles 40. FIG. 13 identifies an area 42 where line segments 46 in adjacent tiles clearly suggest a line structure in the image. Segments 46 in area 44, however, do not have the proximity or angle that would indicate that they are parts of a continuous structure. Another method considers a region of interest (ROI) within the image and examines the gradient at each pixel in the ROI. Gradient strength and angle data can then be accumulated and used to detect lines.

Figure 14:
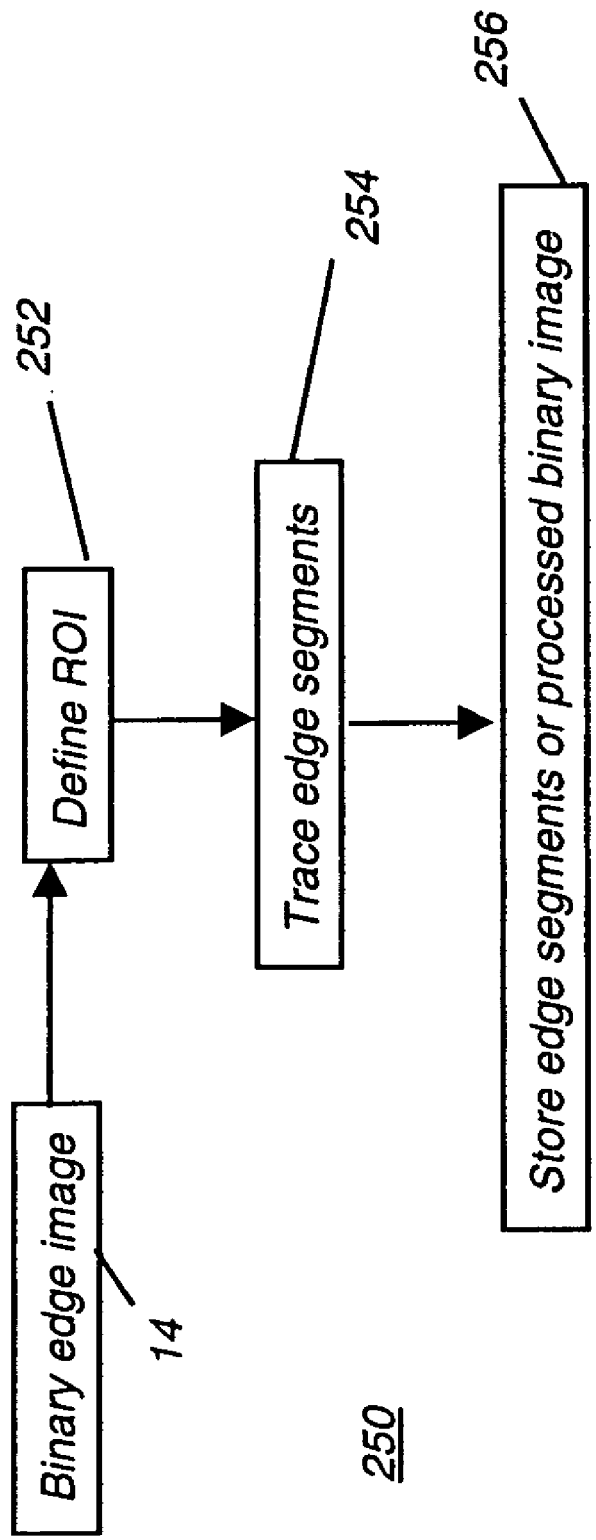
FIG. 14 is a logic flow diagram showing a line segment detection sequence.

FIG. 14 shows the basic sequence of steps for edge tracing in line detection step 250 one embodiment. An ROI definition step 252 is executed, based on prior knowledge of the patient's condition, known tube or tubes, and critical anatomical landmarks or other features. The following steps differ in execution, depending on whether or not tiling is used. Where tiling is utilized, edge tracing algorithms handle each tile independently. In another embodiment, the ROI is identified as area known to contain the tube and having arbitrary dimensions, such as 1200 pixels in height, 600 in width centered around the detected spine area, for example. A tracing step 254 is executed to find continuous line segments over the entire ROI that meet specific threshold characteristics (such as having at least a threshold number of consecutive, adjacent edge pixels). These detected segments are then temporarily stored in a buffer in a storage step 256.

Figure 15:
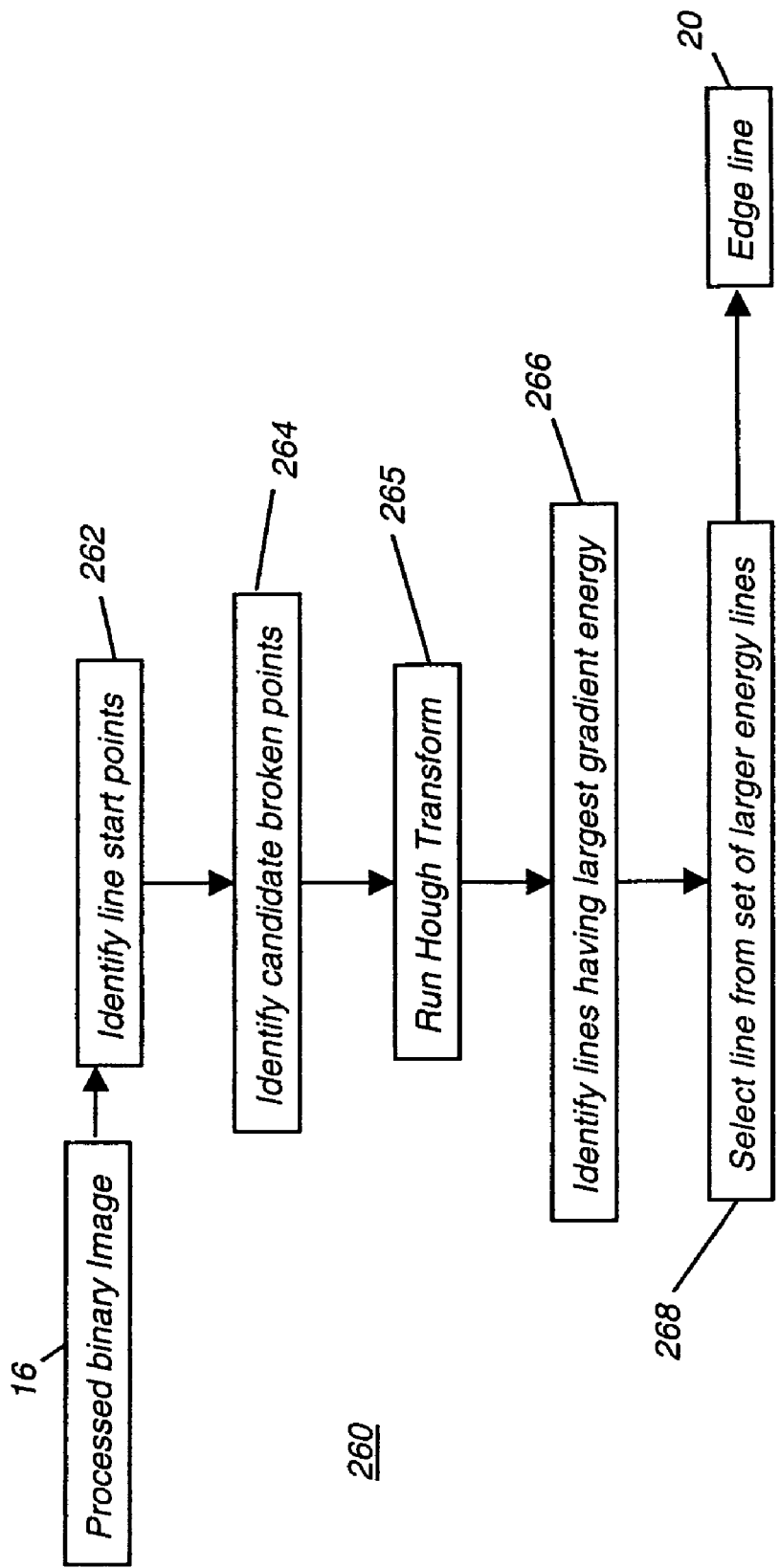
FIG. 15 is a logic flow diagram showing a line edge detection sequence.

In a subsequent line detection step 260, broken lines are detected and can then be reconnected. FIG. 15 shows the logic flow of line detection step 260 in one embodiment, using a Hough Transform. A start point identification step 262 is first executed on processed image 16 to detect terminal points of identified line segments. A broken points identification step 264 follows, in which neighboring segments are associated based on proximity and angle. A Hough transform step 265 is then executed, using the gradient Gx from the end point of each broken line. A line identification step 266 follows, in which the largest gradient energy lines are identified. In a line selection step 268, lines with the nearest angular value and proximity are linked to form an edge line 20.

Double-Edge Detection

Figure 10B:
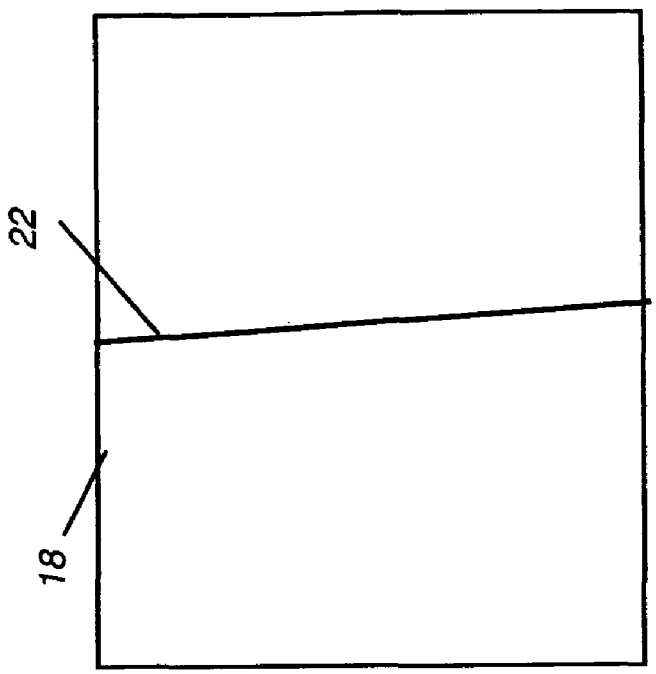
Figure 10A:
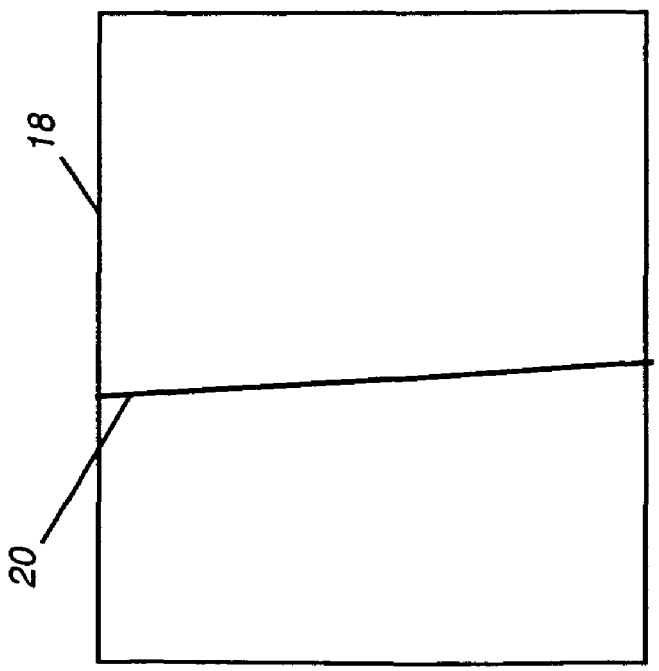

FIGS. 10A, 10B, and 10C show a sequence used for double-edge detection. Using this sequence, a tube 24 is detected by first using line detection steps 250 and 260, as described with reference to FIG. 2, to identify left and right edge lines 20 and 22. Left line 20 of FIG. 10A is obtained using gradient Gx. Right line 22 of FIG. 10B is obtained using the negative gradient −Gx. Left and right edge lines 20 and 22 are paired based on a width value w that is known beforehand for the tube type.

The method of the present invention performs a Hough Transform detection on pairs of lines, thereby executing a "double line" Hough Transform. Criteria for tube detection using this data then use the following information: (i) gradients Gr and −Gr for left and right edge lines 20 and 22; (ii) distance between two edge lines 20 and 22; and (iii) relative angular relationships of line segments of lines 20 and 22.

Figure 16:
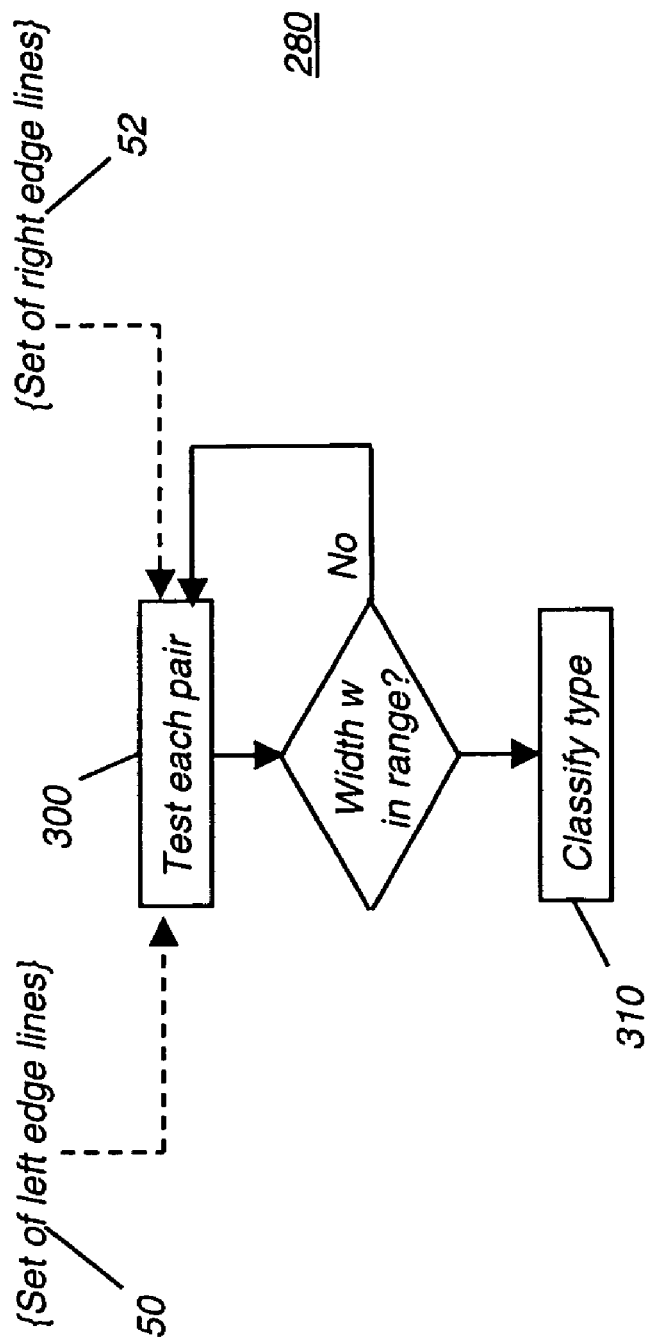
FIG. 16 is a logic flow diagram showing a tube classification sequence.

FIG. 16 shows the sequence used for tube classification step 280 in one embodiment. A set 50 of left edge lines and a set 52 of right edge lines are assembled using edge detection within the region of interest. In a test step 300, each pair consisting of one left and one right edge line is tested to determine if its width w is within the range indicating likelihood that these edges identify a tube. A classification step 310 is then executed to provide a decision on apparent tube type for matched pairs of left and right edges. Other information such as the length of the line and location of the tube/tip relative to anatomic structure can be used for the classification of the tube types.

Figure 17:
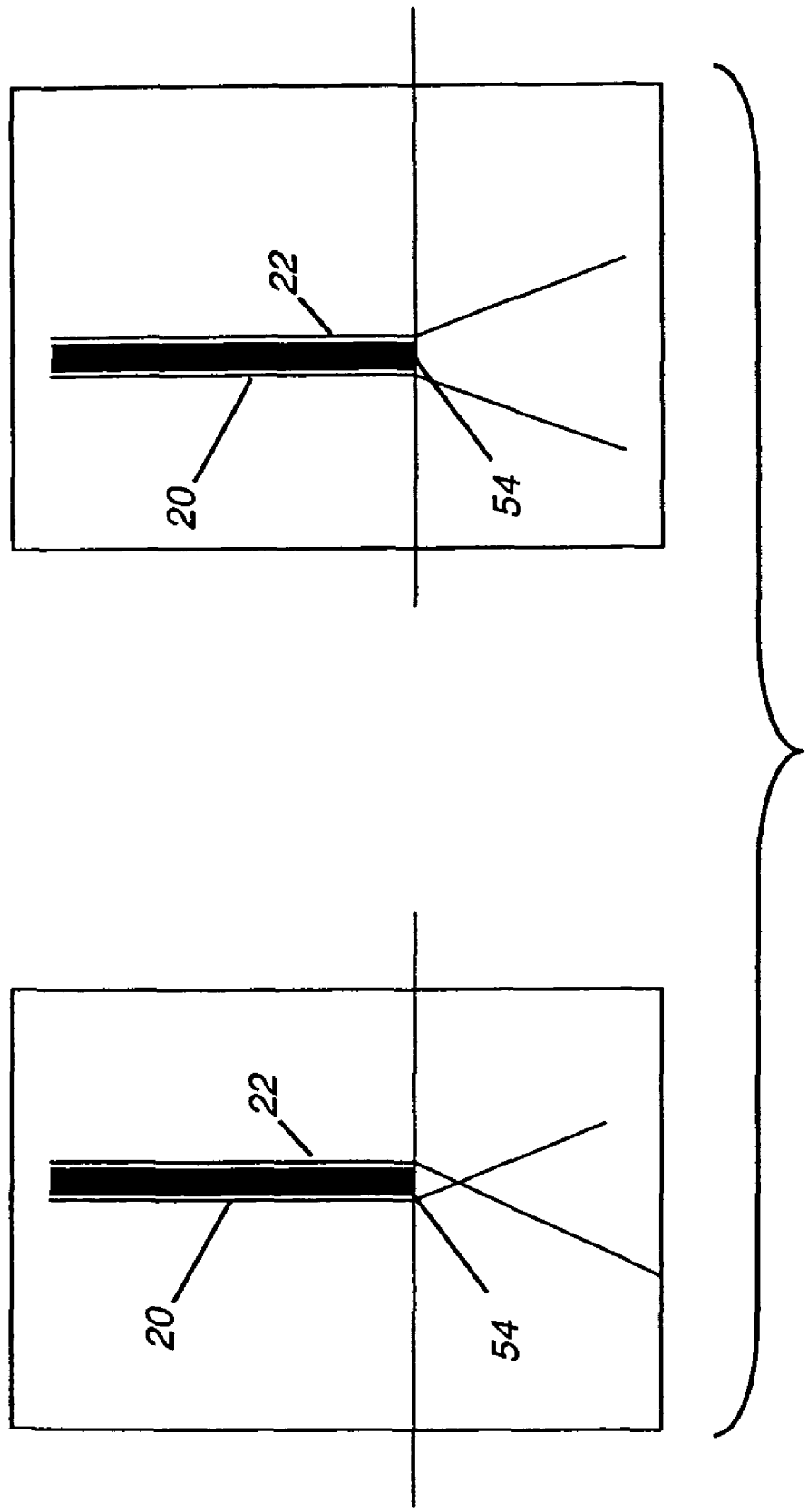
FIG. 17 is a plan view showing tip detection.

FIG. 17 shows how the tip of a tube can be identified using the method of the present invention. Left and right edge lines 20 and 22 either converge or significantly diverge near a tip as shown.

Figure 19A:
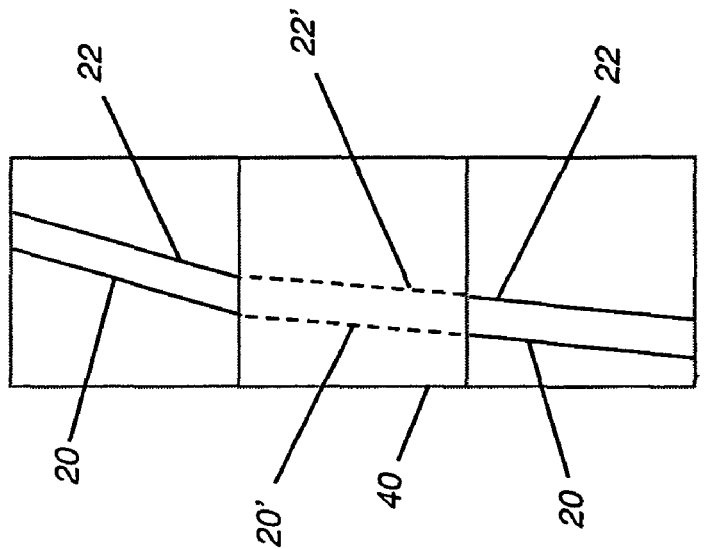
FIGS. 19A and 19B show selection of candidate tube segments for a missing portion.
Figure 19B:
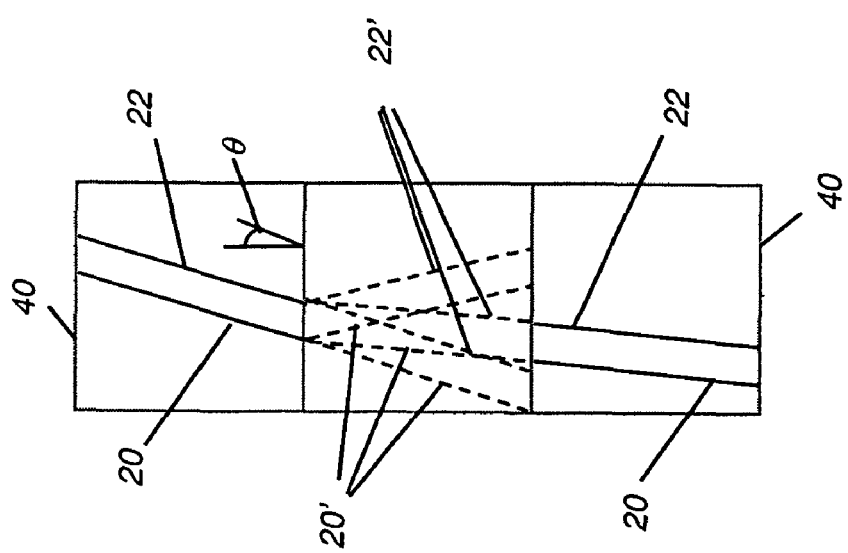

FIGS. 19A and 19B show one example of steps for defining segment in tube detection, forming connected lines from top to bottom. In FIG. 19A, three tiles 40 are shown. Left and right edge lines 20 and 22 have been identified in top and bottom tiles 40. Working from the top, edges are identified in various directions from the ends of positively identified line segments. Candidate left and right edge lines 20' and 22' are indicated in dashed lines. An angle θ from the vertical is defined for this example; other base angles could alternately be used for reference. FIG. 19B shows the selected left and right edge lines 20' and 22' for forming connected lines from the candidate set in FIG. 19A. Similar logic is used for bottom to top detection.

The alternate embodiment shown in FIG. 3 is similar to the basic sequence described above with reference to FIG. 2. One key difference is in a line detection step 251 in which line detection itself is executed using a Hough transform. Other steps for noise removal, image enhancement, edge detection, and tube classification and tip detection remain the same between the embodiments of FIGS. 2 and 3.

Figure 18A:
FIG. 18A is an edge-enhanced image.
Figure 18B:
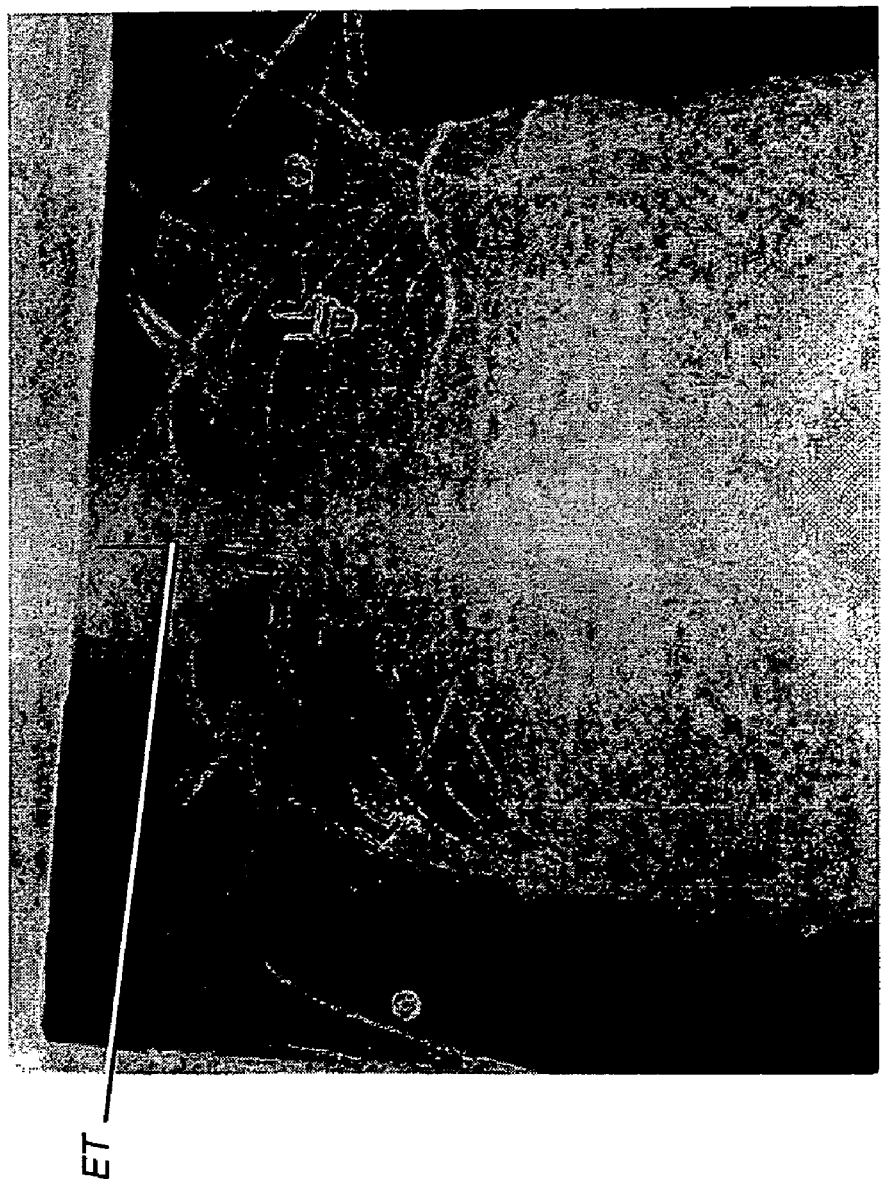
FIG. 18B is an enhanced image showing an ET tube.
Figure 18C:
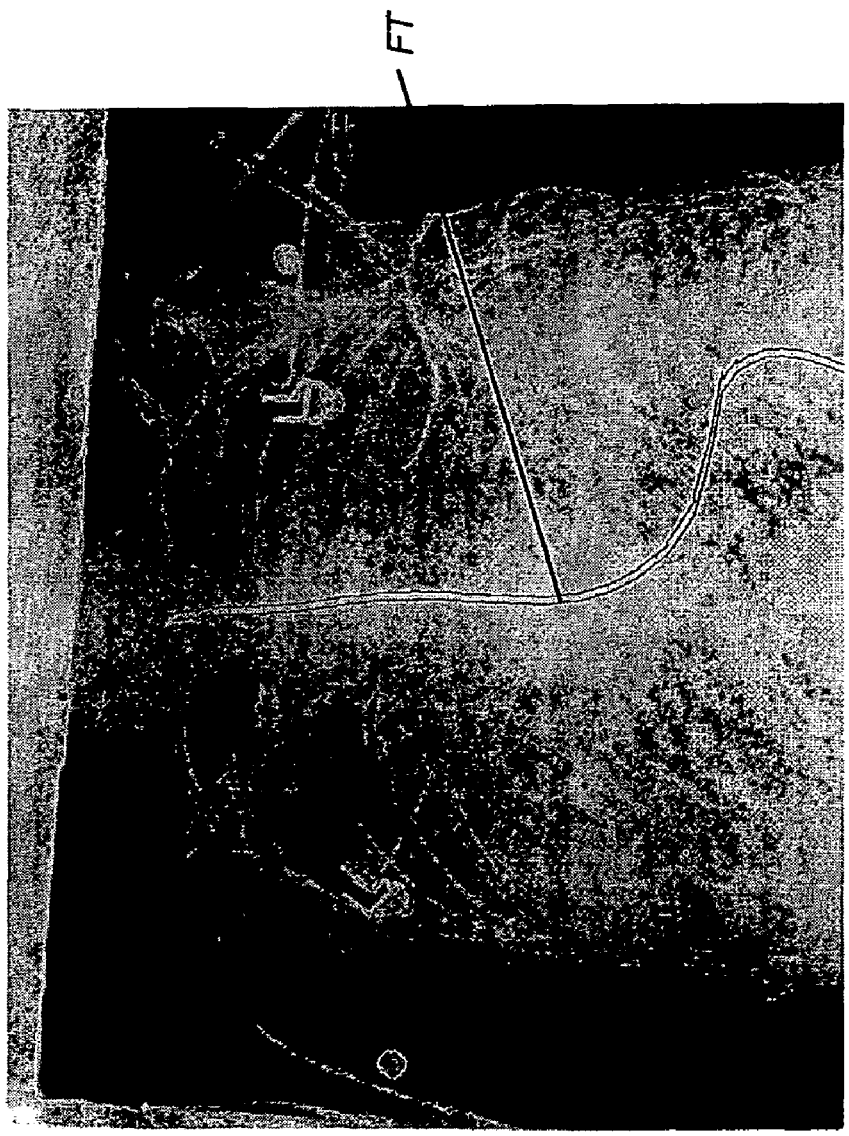
FIG. 18C is an enhanced image showing a feeding tube.
Figure 18D:
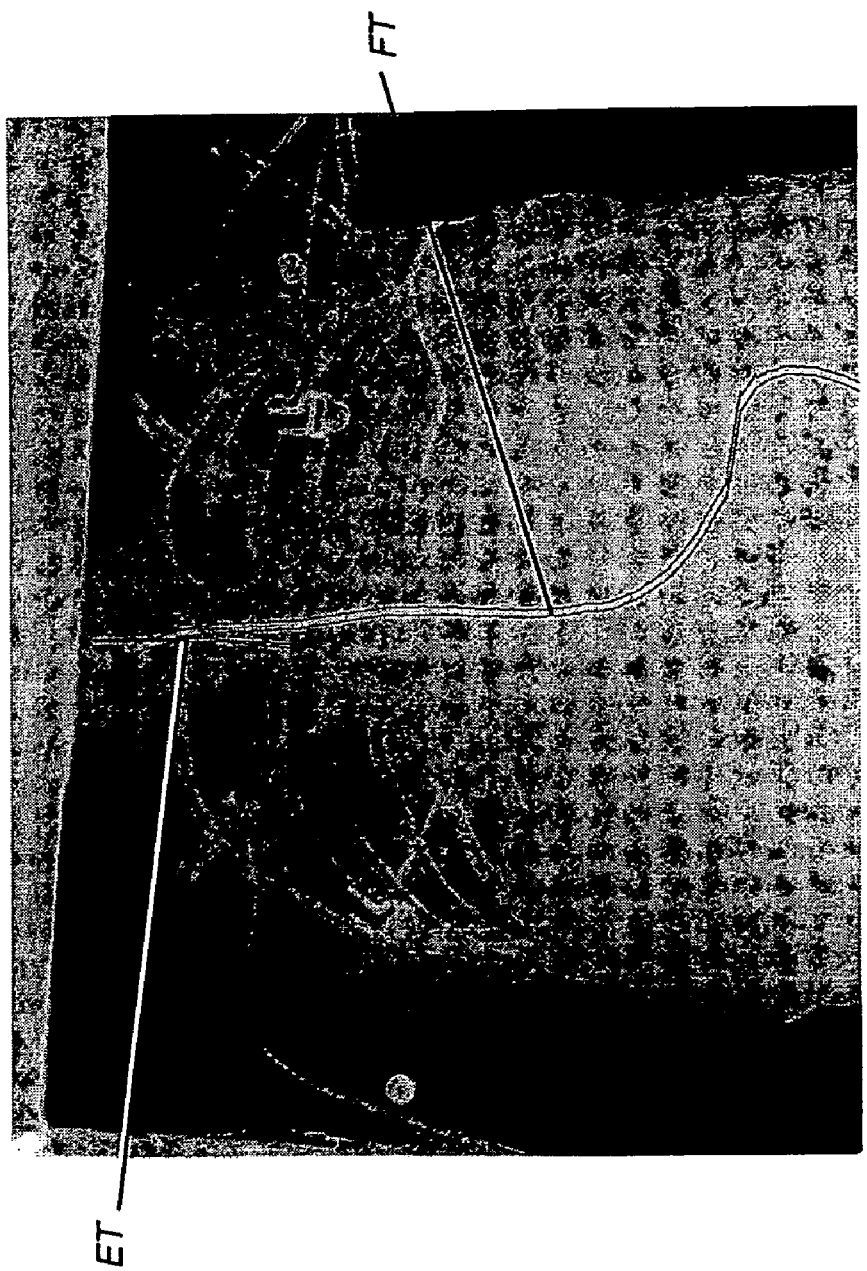
FIG. 18D is an enhanced image showing multiple tubes.

FIGS. 18A through 18D show a sequence of images that illustrate tube detection. FIG. 18A is an edge-enhanced image that is used to show tubing and similar structures with well-defined edges. FIG. 18B shows an ET tube marked on an image. FIG. 18C shows a feeding tube (FT). FIG. 18D shows both ET and FT structures marked on an image. As is clear from the above procedure and examples, it can be helpful to indicate the presence of tubing using superimposed lines on the final image, such as colored lines.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, as noted earlier, any of a number of different methods could be used for line detection. Various algorithms could be applied to the problem of double-edge detection, needed to identify a tube type and needed for tip location. A number of different methods could be applied to the problem of determining the ROI in an individual case, including the use of earlier tube detection results for the same patient.

Thus, what is provided is a method for enhancing diagnostic images in order to detect the position of tubes positioned within the patient.

PARTS LIST

10. Image

12. Enhanced image 14, 16, 18. Image 20, 22, 20', 22'. Edge line

24. Tube 30, 32. Area

34. Tube

36. Tube

40. Tile

42. Area

44. Area

46. Line segment 50, 52. Set

54. Tip

100. Detection method

110. Obtain image step

120. Image processing step

130. Edge detection step

140. Line detection and tracing step

150. Double edge detection step

160. Tip detection step
170. Classification step
180. ROI determination step
200. Detection method
210. Original image
220. Histogram equalization step
230. Noise removal step
232. Noise filtering step
240. Edge detection step
242. Gradient calculation step
244. Edge detection step
250, 251. Line detection step
252. ROI definition step
254. Tracing step
256. Storage step
260. Line detection step
262. Start point identification step
264. Broken points identification step
265. Hough transform step
266. Lines identification step
268. Line selection step
270. Tube detection step
280. Classification step
290. Tip detection step
300. Test step
w. Width
ET. Endo-tracheal tube
FT. Feeding tube
θ. Angle

The invention claimed is:

1. A method for processing a radiographic image, executed at least in part by a processor, comprising:
   obtaining radiographic image data;
   determining a region of interest in the image;
   processing the image to provide edge enhancements and thereby form an edge-enhanced image;
   detecting edge segments in the edge-enhanced image;
   forming connected lines from the edge segments to form a set of connected lines;
   identifying a tube structure by pairing one or more pairs of connected lines that are separated by a width dimension in a predetermined range; and
   detecting a tip for the tube structure according to the convergence or divergence of paired connected lines.

2. The method of claim 1 wherein detecting edge segments comprises using Canny edge detection.

3. The method of claim 1 further comprising applying a Gaussian filter to the image data.

4. The method of claim 1 further comprising highlighting the tube structure and tip outline on the displayed radiographic image.

5. The method of claim 4 wherein highlighting the tube structure and tip outline comprises overlaying a color onto a displayed image.

6. The method of claim 1 wherein identifying the tube structure further comprises classifying the type of tube structure.

7. The method of claim 1 wherein detecting edge segments comprises applying a Hough transform.

8. The method of claim 1 further comprising dividing at least a portion of the image into a plurality of image tiles.

9. The method of claim 1 wherein detecting edge segments comprises computing a gradient.

10. The method of claim 1 wherein identifying a tube structure further comprises forming one or more additional connected pairs of lines to eliminate gaps in the tube structure.

11. The method of claim 1 further comprising performing histogram equalization to enhance grayscale contrast.

12. A method for processing a radiographic image, executed at least in part by a processor, comprising:
    obtaining radiographic image data;
    determining a region of interest in the image;
    processing the image to provide edge enhancement, forming an edge-enhanced image thereby;
    detecting edge segments in the edge-enhanced image;
    pairing edge segments;
    forming connected lines to join disconnected, paired edge segments; and
    detecting a tip according to the convergence or divergence of paired connected lines,
    wherein pairing edge segments further comprises:
    obtaining gradient characteristics for the edge segments;
    calculating the distance between paired edge segments; and
    calculating the relative angles between edge segments.

13. The method of claim 12 further comprising identifying a type of tube according to the distance between paired segments.

14. A method for processing a radiographic image, executed at least in part by a processor, comprising:
    obtaining radiographic image data;
    determining a region of interest in the image;
    processing the image to provide edge enhancement, forming an edge-enhanced image thereby;
    detecting edge segments in the edge-enhanced image;
    pairing edge segments;
    forming connected lines to join disconnected, paired edge segments;
    detecting a tip according to the convergence or divergence of paired connected lines; and
    identifying a tube structure according to a width dimension that separates two paired, connected lines.

15. A method for processing a radiographic image, executed at least in part by a processor, comprising:
    obtaining radiographic image data;
    determining a region of interest in the image;
    detecting edge segments in the region of interest;
    forming connected lines from the edge segments to form a set of connected lines; and
    identifying a tube structure by pairing one or more pairs of connected lines that are separated by a width dimension in a predetermined range.

16. The method of claim 15 further comprising detecting a tip for the tube structure according to the convergence or divergence of paired connected lines.

* * * * *